(12) United States Patent
Jong

(10) Patent No.: US 6,664,409 B1
(45) Date of Patent: Dec. 16, 2003

(54) METHOD FOR THE PREPARATION OF FERROCENY1-1,3-BUTADIENE

(75) Inventor: Shean-Jeng Jong, Tao-Yuan (TW)

(73) Assignee: Chung-Shan Institute of Science & Technology, Tao-Yuan (TW)

( * ) Notice: Subject to any disclaimer, the term of this patent is extended or adjusted under 35 U.S.C. 154(b) by 0 days.

(21) Appl. No.: 10/429,777

(22) Filed: May 6, 2003

(51) Int. Cl.$^7$ ............................ C07F 17/02; B01J 27/06
(52) U.S. Cl. ...................... 556/143; 502/224; 149/19.2
(58) Field of Search ....................... 556/143; 502/224; 149/19.2

(56) References Cited

U.S. PATENT DOCUMENTS

| | | | | | |
|---|---|---|---|---|---|
| 3,739,004 A | * | 6/1973 | Ponder et al. | ............... | 556/143 |
| 3,751,441 A | * | 8/1973 | Van Landuyt | ............... | 556/143 |
| 3,843,426 A | * | 10/1974 | Huskins et al. | ............ | 149/19.2 |
| 6,211,392 B1 | * | 4/2001 | Fang et al. | .................. | 556/143 |

* cited by examiner

*Primary Examiner*—Porfirio Nazario-Gonzalez
(74) *Attorney, Agent, or Firm*—Bacon & Thomas, PLLC

(57) ABSTRACT

Ferrocenaldehyde or ferrocenyl methyl ketone and allyl bromide are reacted in an ether solvent and in the presence of magnesium metal as a catalyst. The liquid portion of the reaction mixture is introduced into a silica gel column, wherein the weak acidity of the silica gel is able to dehydrate the reaction intermediate 1-ferrocenyl-3-buten-1-ol product. The column is eluted with n-hexane, and after evaporating the solvent from the eluate collected, a purified ferrocenyl-1,3-butadiene product is obtained.

7 Claims, No Drawings

METHOD FOR THE PREPARATION OF FERROCENY1-1,3-BUTADIENE

FIELD OF THE INVENTION

The present invention relates to a method for manufacturing ferrocenyl-1,3-butadiene. More particularly, the present invention relates to a method for manufacturing ferrocenyl-1,3-butadiene without heating or vacuum sublimation.

BACKGROUND OF THE INVENTION

U.S. Pat. Nos. 3,739,004 and 3,843,426 disclose that ferrocenyl-1,3-butadiene is a starting material for manufacturing copolymer and homopolymer, which can be employed in applications such as the coating material for aerospace transportation to enhance resistance to photo degradation, ultraviolet rays and gamma rays. Ferrocenyl-1,3-butadiene also can be employed as an enhancement fuel in solid propellant. The fuel of the solid propellant comprises aluminum powder and ammonium perchlorate. Additionally, ferrocenyl-1,3-butadiene not only can be an enhancement fuel in solid propellant but also can decrease binder use.

U.S. Pat. No. 6,211,392B1 discloses a method of manufacturing ferrocenyl-1,3-butadiene, in which a ferrocenecarbonyl is reacted with an allyl halide in a polar aprotic solvent lacking a carbonyl group in the presence of samarium diiodide as a catalyst. The method of this U.S. patent has a relatively high yield; however, the catalyst used, samarium diiodide, is expensive and will undergo hydrolysis in air or moisture.

Several processes for preparing ferrocenyl-1,3-butadiene have been described in the U.S. Pat. No. 6,211,392B1, including the method disclosed in the U.S. Pat. No. 3,739,004, the details of which are incorporated herein by reference.

There is still a need in the industry for developing an easier method for the preparation of ferrocenyl-1,3-butadiene.

SUMMARY OF THE INVENTION

The present invention provide a method for synthesizing ferrocenyl-1,3-butadiene having the following Formula III, which comprises: a) reacting ferrocenecarbonyl having the following Formula I with allyl halide having the following Formula II in an ether solvent and in the presence of magnesium as a catalyst; b) introducing a liquid portion of the resulting reaction mixture into a silica gel column; c) eluting the silica gel column with a solvent of low polarity; d) collecting the resulting eluate from the column; and e) evaporating the solvent from the eluate to a solid comprising ferrocenyl-1,3-butadiene:

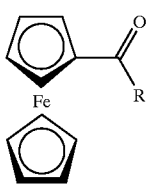

(I)

wherein R is hydrogen or C1–C4 alkyl;

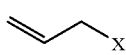

(II)

wherein X is halogen, and preferably X is bromine;

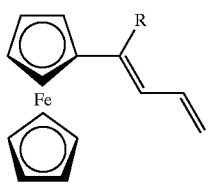

(III)

wherein R is the same as above.

Preferably, the ether solvent is tetrahydrofuran or ethyl ether.

Preferably, said solvent of low polarity is n-hexane.

Preferably, said reaction in step a) is carried out for a period of 1–10 hours at room temperature.

Preferably, said liquid portion is kept in the silica gel column for a period of 1–48 hours in step b).

In the method of the present invention, the reaction mixture in step a) does not need to be heated under refluxing, and the catalyst used in a common alkaline earth metal.

DETAILED DESCRIPTION OF THE INVENTION

A synthesis method for ferrocenyl-1,3-butadiene according to one of the preferred embodiments of the present invention can be represented by the following reaction formula:

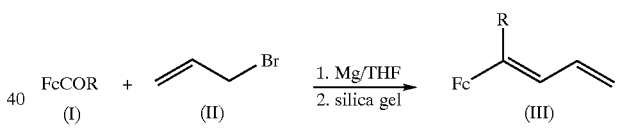

wherein Fc is ferrocenyl, and R is hydrogen or C1–C4 alkyl. Ferrocenecarbonyl (I) reacts with allyl bromide (II) in the presence of magnesium metal as a catalyst and in tetrahydrofuran (THF). The liquid portion of the reaction mixture is introduced into a silica gel column, and is kept in the silica gel column for a certain period of time such that the silica gel having a weak acidity dehydrates the reaction intermediate 1-ferrocenyl-3-buten-1-ol into ferrocenyl-1,3-butadiene (III) having a lower polarity. Next, n-hexane having a low polarity is used to desorb the product (III), and the eluate is collected. After removing the solvent by evaporation, a purified ferrocenyl-1,3-butadiene product is obtained. The silica gel used in the present invention is not limited and can be an arbitrary commercial silica gel. The invented method is simple to be operated and requires no refluxing or vacuuming. Moreover, the catalyst used is stable and is not expensive.

In the method for synthesizing ferrocenyl-1,3-butadiene (III), the amount of the allyl bromide (II) used is 0.1~100 (preferably 1.5) times of the mole number of the ferrocenecarbonyl (I) used. The amount of the magnesium metal used is 0.1~100 (preferably 3) times of the mole number of the ferrocenecarbonyl (I) used. The amount of THF used is 1~1000 L (preferably 15L) per mole of ferrocenecarbonyl (I) used.

The present invention can be further elaborated by way of the following examples which are for illustrative purposes only and not for limiting the scope of the present invention.

EXAMPLE 1

Synthesis of 1-Ferrocenyl-I-methyl-1,3-butadiene 72 mg (3.0 mmole) of magnesium metal was placed in a 50 ml round bottom flask. 228 mg (1.0 mmole) of ferrocenyl methyl ketone and 181.5 mg (1.5 mmole) of allyl bromide were dissolved in 15 ml of THF. The resulting mixture was poured into the round bottom flask containing the magnesium metal while stirring at room temperature for two hours. After two-hour stirring, the cover of the flask was opened, and the liquid portion of the reaction mixture was introduced into a silica gel column, which had been wetted with n-hexane. All the liquid migrated into the silica gel, and the column was placed still for 24 hours. Next, the column was eluated with n-hexane. After evaporating the solvent from the eluate collected from the elution, 230 mg (0.91 mmole) of a purified title product was obtained with a yield of 91%.

$^1$H NMR(300 MHz, CDCl$_3$)δ; 2.11(3H, s, CH3); 4.10(5H, s, Fc); 4.23(2H, s, Fc); 4.40(2H, s, Fc); 5.07(1H, d, J=10.0 Hz, H-4); 5.22(1H, d, J=16.7 Hz, H-4); 6.30(1H, d, J=11.0 Hz, H-2); 6.67(1H, ddd, J=10.0, 11.0, 16.7 Hz, H-3); Elemental analysis: Theoretical value: C, 71.45 H, 6.40; Experimental value: C, 71.57 H, 6.71.

EXAMPLE 2

Synthesis of 1-Ferrocenyl-1,3-butadiene 72 mg (3.0 mmole) of magnesium metal was placed in a 50 ml round bottom flask. 214 mg (1.0 mmole) of ferrocenaldehyde and 181.5 mg (1.5 mmole) of allyl bromide were dissolved in 15 ml of THF. The resulting mixture was poured into the round bottom flask containing the magnesium metal, while stirring at room temperature for two hours. After two-hour stirring, the cover of the flask was opened, and the liquid portion of the reaction mixture was introduced into a silica gel column, which had been wetted with n-hexane. All the liquid migrated into the silica gel, and the column was placed still for 24 hours. Next, the column was eluted with n-hexane. After evaporating the solvent from the eluate collected, 200 mg (0.84 mmole) of a purified title product was obtained with a yield of 84%.

Melting point: 87~88° C.

$^1$H NMR(300 MHz, CDCl$_3$)δ; 4.11(5H, s, fc); 4.23(2H, s, fc); 4.34(2H, s, fc); 5.01–5.05(1H, m, H-4); 5.14–5.20(1H, m, H-4); 6.32–6.43(3H, m, H-1,2,3); Mass: 238(M$^+$).

What is claimed is:

1. A method for synthesizing ferrocenyl-1,3-butadiene having the following Formula III, which comprises: a) reacting ferrocenecarbonyl having the following Formula I with allyl halide having the following Formula II in an ether solvent and in the presence of magnesium as a catalyst; b) introducing a liquid portion of the resulting reaction mixture into a silica gel column; c) eluting the silica gel column with a solvent of low polarity; d) collecting the resulting eluate from the column; e) and evaporating the solvent from the eluate to a solid comprising ferrocenyl- 1,3-butadiene:

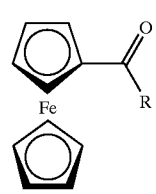

(I)

wherein R is hydrogen or C1–C4 alkyl;

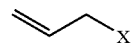

(II)

wherein X is halogen;

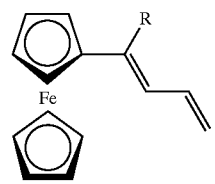

(III)

wherein R is the same as above.

2. The method according to claim 1, wherein X is bromine.

3. The method according to claim 1, wherein the ether solvent is tetrahydrofuran or ethyl ether.

4. The method according to claim 3, wherein the ether solvent is tetrahydrofuran.

5. The method according to claim 1, wherein said solvent of low polarity is n-hexane.

6. The method according to claim 1, wherein said reaction in step a) is carried out for a period of 1–10 hours at room temperature.

7. The method according to claim 1, wherein said liquid portion is kept in the silica gel column for a period of 1–48 hours in step b).

* * * * *